(12) United States Patent
Tobia

(10) Patent No.: US 9,555,012 B2
(45) Date of Patent: Jan. 31, 2017

(54) METHODS FOR MAINTAINING OR IMPROVING HEALTH, WELL-BEING AND/OR A PHYSIOLOGICAL FUNCTION IN A SUBJECT

(71) Applicant: DYNAMIS THERAPEUTICS, INC., Jenkintown, PA (US)

(72) Inventor: Annette Tobia, Wyndmoor, PA (US)

(73) Assignee: Dynamis Therapeutics, Inc., Jenkintown, PA (US)

( * ) Notice: Subject to any disclaimer, the term of this patent is extended or adjusted under 35 U.S.C. 154(b) by 0 days.

(21) Appl. No.: 13/962,645

(22) Filed: Aug. 8, 2013

(65) Prior Publication Data

US 2014/0045947 A1 Feb. 13, 2014

Related U.S. Application Data

(60) Provisional application No. 61/681,241, filed on Aug. 9, 2012, provisional application No. 61/770,553, filed on Feb. 28, 2013.

(51) Int. Cl.
*A61K 31/133* (2006.01)
*A61K 31/155* (2006.01)

(52) U.S. Cl.
CPC ........... *A61K 31/133* (2013.01); *A61K 31/155* (2013.01)

(58) Field of Classification Search
CPC combination set(s) only.
See application file for complete search history.

(56) References Cited

U.S. PATENT DOCUMENTS

| | | | |
|---|---|---|---|
| 2007/0021357 A1* | 1/2007 | Tobia | A61K 31/4152 514/23 |
| 2009/0042967 A1* | 2/2009 | Hasuoka | 514/409 |
| 2010/0297046 A1 | 11/2010 | Schwartz et al. | |
| 2011/0112188 A1 | 5/2011 | Tobia et al. | |
| 2011/0166228 A1 | 7/2011 | Holmeide et al. | |
| 2012/0302540 A1* | 11/2012 | Ambarkhane et al. | 514/210.02 |
| 2014/0011814 A1 | 1/2014 | Mylari et al. | |
| 2014/0045947 A1 | 2/2014 | Tobia | |

OTHER PUBLICATIONS

Layegh et., Systemic Meglumine Antimoniate in Acute Cutaneous Leishmaniasis: Children versus Adults, 2011, Am. J. Trop. Med. Hyg., vol. 84, No. 4, pp. 539-542.*
International Search Report & Written Opinion dated Apr. 17, 2014 for PCT International Application No. PCT/US2013/054160.

\* cited by examiner

*Primary Examiner* — Kortney L Klinkel
*Assistant Examiner* — Tori M Strong
(74) *Attorney, Agent, or Firm* — The Webb Law Firm

(57) ABSTRACT

The invention relates to a method of treating or preventing a condition in a subject, comprising administering to the subject an acceptable composition comprising meglumine or a salt thereof. The invention further relates to a method of improving a physiological function in a subject, comprising administering to the subject an acceptable composition comprising meglumine or a salt thereof.

16 Claims, 8 Drawing Sheets

METHODS FOR MAINTAINING OR IMPROVING HEALTH, WELL-BEING AND/OR A PHYSIOLOGICAL FUNCTION IN A SUBJECT

CROSS-REFERENCE TO RELATED APPLICATIONS

The present application claims priority under 35 U.S.C. §119(e) to U.S. Provisional Applications No. 61/770,553, filed Feb. 28, 2013, and No. 61/681,241, filed Aug. 9, 2012, all of which applications are hereby incorporated by reference in their entireties herein.

BACKGROUND OF THE INVENTION

Health is the level of functional or metabolic efficiency of a living being. In humans, health is the general condition of a person's mind, body and spirit, usually meaning to be free from illness, injury or pain (as in "good health," "good state of health" or "healthy"). According to the World Health Organization (WHO), health is "a state of complete physical, mental, and social well-being and not merely the absence of disease or infirmity" (World Health Organization, Constitution of the World Health Organization—Basic Documents, 45$^{th}$ edition, Supplement, October 2006). The maintenance and promotion of health is achieved through different combination of physical, mental, and social well-being, together sometimes referred to as the "health triangle" (Nutter, 2003, The Health Triangle, Anchor Points, Inc.).

A nutraceutical (a portmanteau of the words "nutrition" and "pharmaceutical") is a supplement, food or food product that reportedly provides health benefits. Such products may range from isolated nutrients, dietary supplements and specific diets to genetically engineered foods, herbal products, and processed foods such as cereals, soups, and beverages.

There is a need in the art for novel methods for improving the overall health or well-being of a subject. In one aspect, such a method should be effective in treating or preventing conditions that affect the subject, including effects of aging. In another aspect, such a method should be effective in affecting or improving physiological functions known to correlate with an overall good state of health or well-being in the subject. The present invention satisfies this need.

BRIEF SUMMARY OF THE INVENTION

The invention includes a method of ameliorating or preventing weight gain, promoting weight control, or promoting weight loss in a subject in need thereof. The method comprises administering to the subject an effective amount of a composition comprising meglumine or a salt thereof; whereby weight gain in the subject is ameliorated or prevented, or weight control or weight loss in the subject is promoted.

The invention also includes a method of treating or preventing disregulation of blood glucose levels in a subject in need thereof. The method comprises administering to a subject an effective amount of a composition comprising meglumine or a salt thereof; whereby disregulation of blood glucose levels in the subject is treated or prevented.

The invention further includes a method of treating or preventing muscle weakness or increasing muscle strength in a subject in need thereof. The method comprises administering to a subject an effective amount of a composition comprising meglumine or a salt thereof; whereby muscle weakness in the subject is treated or prevented, or muscle strength in the subject is increased.

The invention also includes a method of reducing or preventing the increase of triglyceride levels in a subject in need thereof. The method comprises administering to a subject an effective amount of a composition comprising meglumine or a salt thereof; whereby the increase of triglyceride levels in the subject is reduced or prevented.

In one embodiment, the subject is further administered medication to treat symptoms of diabetes.

The invention further includes a method of reducing or preventing the increase of LDL levels in a subject in need thereof. The method comprises administering to a subject an effective amount of a composition comprising meglumine or a salt thereof; whereby the increase of LDL levels in the subject is reduced or prevented.

In one embodiment, the subject is further administered medication to treat symptoms of diabetes.

The invention also includes a method of reducing or preventing the increase of total cholesterol levels in a subject in need thereof. The method comprises administering to a subject an effective amount of a composition comprising meglumine or a salt thereof; whereby the increase of total cholesterol levels in the subject is reduced or prevented.

In one embodiment, the subject is further administered medication to treat symptoms of diabetes.

The invention further includes a method of reducing or preventing the increase of levels of a lipoprotein particle or apolipoprotein in a subject in need thereof. The method comprises administering to a subject an effective amount of a composition comprising meglumine or a salt thereof; whereby the increase of levels of the lipoprotein particle or apolipoprotein in the subject is reduced or prevented.

In one embodiment, the lipoprotein particle or apolipoprotein comprises Apo B, LDL-P, sdLDL, Apo A-I or any combinations thereof. In another embodiment, the lipoprotein particle or apolipoprotein comprises Apo B, and the Apo B:Apo A-I ratio in the subject is reduced. In yet another embodiment, the subject is further administered medication to treat symptoms of diabetes.

The invention also includes a method of increasing or preventing the reduction of creatine/albumin levels in a subject in need thereof. The method comprises administering to a subject an effective amount of a composition comprising meglumine or a salt thereof, whereby the creatine/albumin levels in the subject are increased or the reduction of the creatine/albumin levels in the subject is prevented.

The invention further includes a method of increasing longevity or promoting anti-aging effects in a subject in need thereof. The method comprises administering to a subject an effective amount of a composition comprising meglumine or a salt thereof, whereby longevity in the subject is increased.

The invention also includes a method of improving the skin condition in a subject in need thereof. The method comprises administering to a subject an effective amount of a composition comprising meglumine or a salt thereof; whereby the skin condition in the subject is improved.

The invention further includes a method of improving sexual stamina or performance in a subject in need thereof. The method comprises administering to a subject an effective amount of a composition comprising meglumine or a salt thereof; whereby sexual stamina or performance in the subject is improved.

The invention also includes a method of increasing vitality or energy levels in a subject in need thereof. The method comprises administering to a subject an effective amount of a composition comprising meglumine or a salt thereof; whereby vitality or energy levels in the subject are increased.

The invention further includes a method of improving the mental capacity, or ameliorating or preventing the onset of dementia, in a subject in need thereof. The method comprises administering to a subject an effective amount of a composition comprising meglumine or a salt thereof; whereby the mental capacity is improved, or the onset of dementia in the subject is ameliorated or prevented.

The invention also includes a method of improving or maintaining kidney function in a subject in need thereof. The method comprises administering to a subject an effective amount of a composition comprising meglumine or a salt thereof; whereby kidney function in the subject is improved or maintained.

In one embodiment, the composition is administered to the subject by a route selected from the group consisting of inhalational, oral, rectal, vaginal, parenteral, topical, transdermal, pulmonary, intranasal, buccal, ophthalmic, intrathecal, parenteral, intravenous, and any combinations thereof. In another embodiment, the composition is administered to the subject at a frequency selected from the group consisting of once a day, twice a day, three times a day, four times a day, once a week, twice a week, three times a week, four times a week, once a month, twice a month, and any combinations thereof. In yet another embodiment, the composition is administered to the subject at a dosage ranging from about 1 ng/kg/application to about 100 g/kg/application. In yet another embodiment, the composition is administered to the subject at a dosage ranging from about 1 ng/kg/application to about 100 mg/kg/application. In yet another embodiment, the composition is administered to the subject as a controlled-release formulation. In yet another embodiment, the subject is a mammal. In yet another embodiment, the mammal is a human.

The invention further includes a composition comprising meglumine or a salt thereof and a first amount of a sweet-tasting compound, wherein the composition is suitable for oral consumption by a subject; wherein the sweetness of the composition is equivalent to the sweetness of a second amount of the sweet-tasting compound, further wherein the composition is healthier, is less toxic or has fewer undesirable physiological effects in the subject than the second amount of the sweet-tasting compound.

In one embodiment, the sweet-tasting compound comprises glucose, dextrose, high-fructose corn syrup, mannitol, sorbitol, stevia, xylitol, acesulfame potassium, alitame, aspartame, a salt of aspartame-acesulfame, cyclamate, dulcin, glucin, neohesperidin dihydrochalcone, neotame, saccharin, sucralose, or any combinations thereof. In another embodiment, the subject is a mammal. In yet another embodiment, the mammal is a human.

The invention also includes a composition comprising meglumine or a salt thereof and a therapeutic agent selected from the group consisting of α-glucosidase inhibitors, lipase inhibitors, sulfonyl ureas, meglitinides, biguanides, thiazolidinediones, pramlintide, incretin mimetics, DPP-IV inhibitors, a salt thereof, and any combinations thereof. In one embodiment, the therapeutic agent comprises metformin.

BRIEF DESCRIPTION OF THE DRAWINGS

The following detailed description of preferred embodiments of the invention is better understood when read in conjunction with the appended drawings. For the purpose of illustrating the invention, there are shown in the drawings embodiments that are presently preferred. It should be understood, however, that the invention is not limited to the precise arrangements and instrumentalities of the embodiments shown in the drawings.

DETAILED DESCRIPTION OF THE INVENTION

Figure 1:
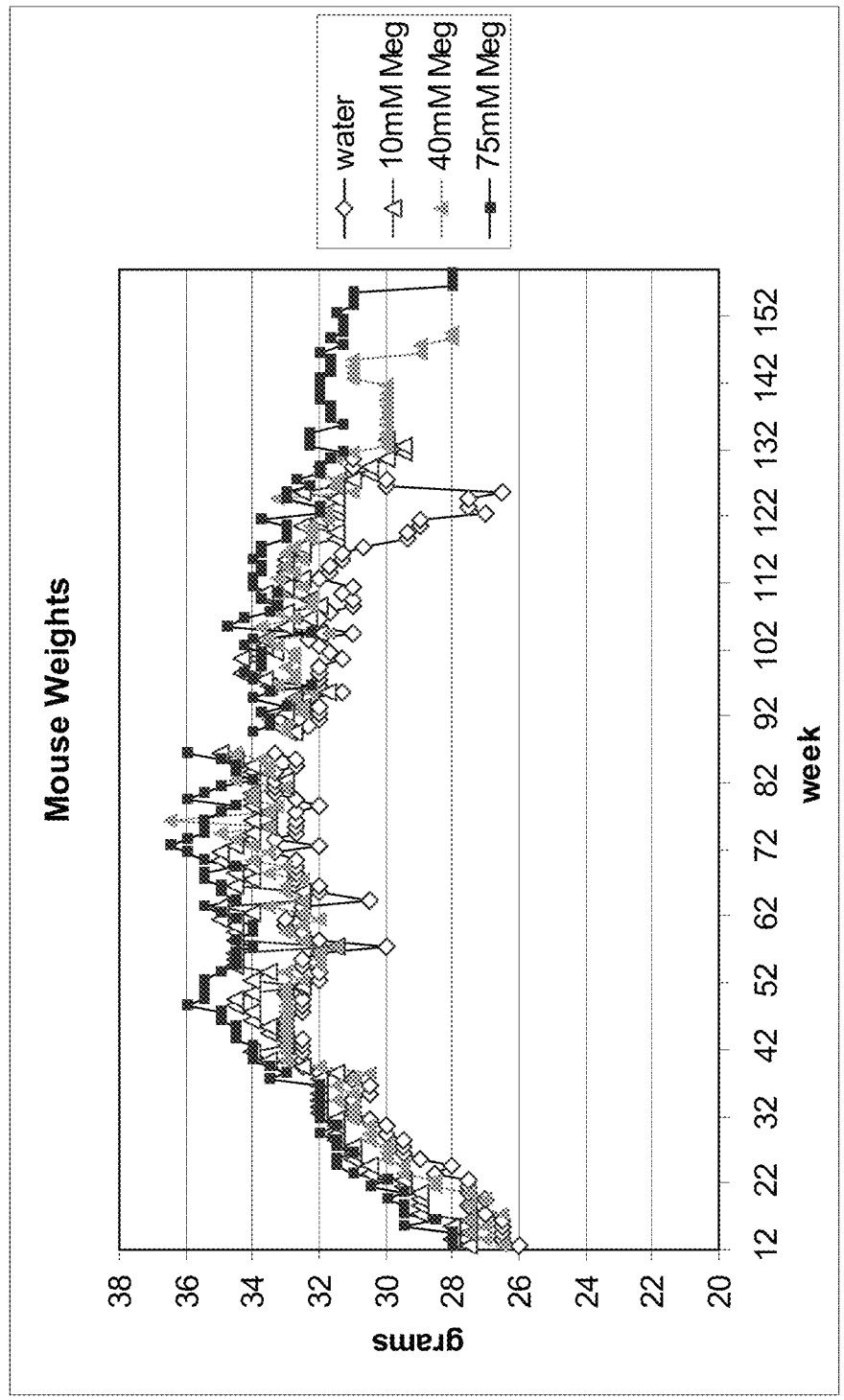
FIG. 1 is a graph illustrating the average weight of mice treated with various doses of meglumine, as a function of time.

The present invention relates to the unexpected discovery that administering meglumine (also known as N-methylglucamine, or (2R,3R,4R,5S)-6-methylaminohexane-1,2,3,4,5-pentol) or a salt thereof to a subject results in improvement of the overall state of health of the subject. In one aspect, administering meglumine to the subject mitigates, reverses or prevents a physiological condition associated with a poor state of health or well-being of the subject (i.e., an unhealthy physiological condition), such as, but not limited to, unwanted weight gain, disregulated blood glucose, muscle weakness, low energy level, high triglyceride levels, low creatine/albumin levels, or any combinations thereof. In another aspect, administering meglumine to the subject improves a physiological function associated with an overall good state of health or well-being of the subject, such as, but not limited to, longevity, sexual performance, vitality, energy level, mental capacity, delay of dementia onset, or any combinations thereof. The invention thus contemplates compositions comprising meglumine or a salt thereof to improve the subject's overall state of health as discussed herein.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, a "subject" or "individual" or "patient" may be a human or non-human mammal. Non-human mammals include, for example, livestock and pets, such as ovine, bovine, porcine, canine, feline and murine mammals. Preferably, the subject is human.

As used herein, the term "physiological function" refers to a marker, function, characteristic or parameter, which correlates with the overall state of health or well-being of a subject. The physiological function may be measured objectively or subjectively.

As used herein, the term "physiological condition" refers to a condition, diagnosis or parameter determined in or characteristic of a subject. The physiological condition may be measured objectively or subjectively.

As used herein, the term "anti-aging effects" as associated with a compound refers to the capacity of the compound to eliminate or minimize the effects of aging in a subject, such as loss of energy and stamina, and development of age-related conditions. "Anti-aging effects" also refers to the ability of a compound to extend the life of the subject over the applicable life expectancy.

As used herein, "an unhealthy condition" refers to a state of health of an animal wherein the animal cannot maintain homeostasis, and wherein if the condition is not ameliorated then the animal's health continues to deteriorate.

As used herein, "an unhealthy condition" in an animal also refers to a state of health in which the animal is able to maintain homeostasis, but in which the animal's state of health is less favorable than it would be in the absence of the condition. Left untreated, a condition does not necessarily cause a further decrease in the animal's state of health.

As used herein, a "normal" subject with respect to the condition does not present the characteristic, symptoms or effects of the condition.

As used herein, a "normal" subject with respect to the physiological function presents a physiological function that correlates with a healthy status.

As used herein, the term "binding" refers to the adherence of molecules to one another, such as, but not limited to, enzymes to substrates, ligands to receptors, antibodies to antigens, DNA binding domains of proteins to DNA, and DNA or RNA strands to complementary strands.

As used herein, the term "biological sample" refers to samples obtained from a subject, including skin, hair, tissue, blood, plasma, cells, sweat and urine.

As used herein, a "compound" refers to one or more chemical entities, each of which may independently be isolated from nature or synthesized.

As used herein, an "instructional material" includes a publication, a recording, a diagram, a video, or any other medium of expression that may be used to communicate the usefulness of the compositions useful within the invention in the kit for preventing or treating the various conditions recited herein, or improving the physiological functions recited herein. Optionally or alternately, the instructional material may describe one or more methods of alleviating or treating the conditions or improving the physiological functions in a cell or a tissue of a mammal. The instructional material of the kit of the invention may, for example, be affixed to a container that contains a composition useful within the invention or be shipped together with a container that contains a composition useful within the invention. Alternatively, the instructional material may be shipped separately from the container with the intention that the instructional material and a composition useful within the invention be used cooperatively by the recipient.

As used herein, the term "skin" refers to the commonly used definition of skin, e.g., the epidermis and dermis, and the cells, glands, and connective tissue which comprise the skin.

As used herein, the term "treatment" or "treating" is defined as the application or administration of a composition useful within the invention (alone or in combination with another agent), to a subject, or application or administration of a composition useful within the invention to an isolated tissue or cell line from a subject (for example, for diagnosis or ex vivo applications), who has an unhealthy physiological condition contemplated herein, a symptom of or the potential to develop an unhealthy physiological condition contemplated herein, with the purpose to prevent, cure, heal, alleviate, relieve, alter, remedy, ameliorate, improve or affect an unhealthy physiological condition contemplated herein, the symptoms of or the potential to develop an unhealthy physiological condition contemplated herein. Similar considerations apply to improving the physiological functions or parameters contemplated within the invention. Such treatments may be specifically tailored or modified, based on knowledge obtained from the field of pharmacogenomics.

As used herein, "alleviating a condition," means reducing the severity of the symptom of the condition.

As used herein, a "prophylactic" treatment is a treatment administered to a subject who does not exhibit signs of a condition or exhibits only early signs of the condition for the purpose of decreasing the risk of developing pathology associated with the condition.

As used herein, the term "prevent" or "prevention" means no condition development if none had occurred, or no further condition development if there had already been development of the condition. Also considered is the ability of one to prevent some or all of the symptoms associated with the condition.

As used herein, the term "treat" means reducing the frequency with which symptoms are or may be experienced by a patient or subject or administering a compound to reduce the severity with which symptoms are or may be experienced. An appropriate amount of the compound in any individual case may be determined by one of ordinary skill in the art using routine experimentation.

As used herein, the term "effective amount" of a compound or composition refers to the amount of the compound or composition that is sufficient to provide a beneficial effect to the subject to which the compound or composition is administered.

As used herein, the term "acceptable" refers to a material, such as a carrier or diluent, which does not abrogate the biological activity or properties of the compound or composition, and is relatively non-toxic, i.e., the material may be administered to an individual without causing undesirable biological effects or interacting in a deleterious manner with any of the components of the composition in which it is contained.

As used herein, the language "acceptable salt" refers to a salt of the administered compounds prepared from acceptable non-toxic acids, including inorganic acids, organic acids, solvates, hydrates, or clathrates thereof.

As used herein, the term "composition" refers to a mixture of at least one compound useful within the invention with other chemical components, such as carriers, stabilizers, diluents, dispersing agents, suspending agents, thickening agents, and/or excipients. The composition facilitates administration of the compound to an organism. Multiple techniques of administering a compound exist in the art including, but not limited to: intravenous, oral, aerosol, parenteral, ophthalmic, pulmonary and topical administration. In one embodiment, the composition is non-toxic.

The language "acceptable carrier" includes an acceptable salt, acceptable material, composition or carrier, such as a liquid or solid filler, diluent, excipient, solvent or encapsulating material, involved in carrying or transporting a compound(s) of the present invention within or to the subject such that it may perform its intended function. The acceptable carrier is preferably non-toxic. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in non-toxic formulations, or any combination thereof. As used herein, "acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

The term "standard," as used herein, refers to something used for comparison. For example, it can be a known standard agent or compound administered and used for comparing results when administering a test compound, or it can be a standard parameter or function measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

Compositions

The invention includes a composition comprising meglumine or a salt thereof and a first amount of a sweet-tasting compound, wherein the composition is suitable for oral consumption by a subject; wherein the sweetness of the composition is equivalent to the sweetness of a second amount of the sweet-tasting compound, further wherein the composition is healthier, is less toxic or has fewer undesirable physiological effects in the subject than the second amount of the sweet-tasting compound.

In one embodiment, the sweet-tasting compound comprises glucose, dextrose, high-fructose corn syrup, mannitol, sorbitol, stevia, xylitol, acesulfame potassium, alitame, aspartame, a salt of aspartame-acesulfame, cyclamate, dulcin, glucin, neohesperidin dihydrochalcone, neotame, saccharin, sucralose, or any combinations thereof. In another embodiment, the subject is a mammal. In yet another embodiment, the mammal is a human.

The invention includes a composition comprising meglumine or a salt thereof and a therapeutic agent selected from the group consisting of α-glucosidase inhibitors, lipase inhibitors, sulfonyl ureas, meglitinides, biguanides, thiazolidinediones, pramlintide, incretin mimetics, DPP-IV inhibitors, HSGLT2 inhibitor, a salt thereof, and any combinations thereof. In one embodiment, the therapeutic agent comprises metformin.

In one aspect, a composition comprising meglumine or a salt thereof and a therapeutic agent is contemplated within the invention. Such composition is useful in mitigating, reversing or preventing a physiological condition associated with a poor state of health or well-being of the subject (i.e., an unhealthy physiological condition), such as, but not limited to, unwanted weight gain, disregulated blood glucose, high triglyceride levels, low creatine/albumin levels, or any combinations thereof. In one embodiment, the therapeutic agent is used to treat symptoms of diabetes in a subject in need thereof. In another embodiment, the diabetes is type 2 diabetes.

Non-limiting examples of therapeutic agents contemplated within the invention are:

α-glucosidase inhibitors: inhibit upper GI enzymes (α-glucosidases) responsible for digesting carbohydrates, slowing absorption of glucose; also cause slower rise in postprandial blood glucose concentrations. Non-limiting examples: acarbose (Precose, Glucobay); miglitol (Glyset); voglibose (Vogseal, Volix, Basen).

lipase inhibitors: inhibit pancreatic and gastric lipases, blocking fat absorption. Non-limiting examples: orlistat (Xenical, Alli).

sulfonyl ureas: act as insulin secretagogues, triggering insulin release by interacting with the ATP-dependent potassium channel of the pancreatic β-cells. The net result is that more insulin is released at all blood glucose concentrations. They are the most commonly used drugs for treatment of patients with type 2 diabetes, but, since they trigger release of insulin itself, the combination of insulin & sulfonyl ureas is not common. Non-limiting examples: $1^{st}$ generation of sulfonyl ureas—acetohexamide, chlorpropamide (Diabinese), tolbutamide (Orinase), tolazamide; $2^{nd}$ generation of sulfonyl ureas—gliclazide (Diamicron R, Diamicron MR), glyburide or glibenclamide (Diabeta, Micronase, Glynase), glipizide (Glucotrol, Glucotrol XL), glimepiride (Amaryl), gliquidone (Glurenorm).

meglitinides: short-acting glucose-lowering drugs, acting by regulating ATP-dependent potassium channels in pancreatic β-cells like sulfonyl ureas; structurally different from sulfonylureas and act via different receptors as well. Non-limiting examples: mitiglinide (Glufast); nateglinide (Starlix); repaglinide (Prandix).

biguanides: reduce glucose release from the liver and increase glucose uptake by skeletal muscle. Metformin is the preferred initial treatment of type 2 diabetes, with good glycemic efficacy, absence of weight gain and hypoglycemia, general tolerability and low cost. The combination of metformin & insulin is generally associated with lower weight gain than insulin by itself or the combination of insulin & sulfonylureas. The triple combination of a sulfonyl urea, metformin and insulin glargine has been shown to have fewer adverse effects, fewer lipid profile problems and lower cost than the triple combination of a sulfonyl urea, metformin and rosiglitazone. Non-limiting examples: metformin (Glucophage); phenformin (DBI); buformin (Glybigid, Glybigidum).

thiazolidinediones: increase insulin sensitivity by acting on adipose, muscle and liver tissue to increase glucose utilization and decrease glucose production. The mechanism of action is not fully understood, but they seem to bind and activate one or more peroxisome proliferator-activated receptors (PPARs), regulating gene expression. Non-limiting examples: rosiglitazone (Avandia); pioglitazone (Actos); troglitazone (Rezulin); tesaglitazar (Pargluva).

pramlintide (Symlin): also known as islet amyloid polypeptide, is a synthetic analog of human amylin that slows gastric emptying and suppresses glucagon, reducing postprandial rises in blood glucose levels; approved by the FDA to lower blood sugar in type 1 diabetes patients.

incretin mimetics: these insulin secretagogues act as glucagon-like peptide-1 (GLP-1) membrane-receptor agonists. They act in a glucose-dependent manner, stimulating insulin secretion only when blood glucose levels are higher than normal. They also promote β-cell regeneration in animal models. Incretin mimetics decrease gastric motility and cause nausea. Non-limiting examples: exenatide, exedin-4 or AC2993 (Byetta); liraglutide, NN2211, or NNC 90-1170; it consists of a lipid conjugate of GLP-1, with high protein binding and a half-life of ~10 h in man.

DPP-IV inhibitors: affect glucose regulation, inhibiting degradation of GLP-1. They generally cause fewer problems with hypoglycemia or weight gain as compared to standard treatments. Non-limiting examples: sitagliptin (Januvia); sitagliptin & metformin (Janumet); vildagliptin (Galvus); vildagliptin & metformin (Eucreas).

Sodium-glucose cotransporter 2 (SGLT2) inhibitors: cause a substantial increase in the amount of glucose that flows out in the urine, thus decreasing blood glucose levels. They act to control glucose in an insulin-independent manner. Non-limiting example is dapagliflozin (Forxiga).

In one aspect, the at least one additional compound is selected from the group consisting of vitamin D, vitamin B complex, vitamin E, vitamin C, ascorbic acid, hyaluronic acid (e.g., 1.2 million Dalton), vitamin B complex, L-carnitine, creatine, lycine, taurine, L-arginine, resveratrol, a salt thereof, and any combinations thereof.

In one embodiment, meglumine and the at least one additional compound have synergistic properties within the methods of the invention. A synergistic effect may be calculated, for example, using suitable methods such as, for example, the Sigmoid-Emax equation (Holford & Scheiner, 1981, Clin. Pharmacokinet 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the compound combination. The corresponding graphs associated with the equations referred to above are the concentration-effect curve, isobologram curve and combination index curve, respectively.

Salts

A composition comprising meglumine or a salt thereof is contemplated within the invention. Meglumine, or other compounds contemplated within the invention, may form salts with acids, and such salts are included in the present invention. In one embodiment, the salts are acceptable non-toxic salts. The term "salts" embraces addition salts of free acids useful within the methods of the invention. The term "acceptable salt" refers to salts that possess toxicity profiles within a range that affords utility in in vivo applications. Unacceptable salts may nonetheless possess properties such as high crystallinity, which have utility in the practice of the present invention, such as for example utility in process of synthesis, purification or formulation of compounds useful within the methods of the invention.

Suitable acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Other compounds contemplated within the invention may form salts with bases. Suitable acceptable base addition salts of compounds useful within the invention include, for example, metallic salts including alkali metal, alkaline earth metal and transition metal salts such as, for example, calcium, magnesium, potassium, sodium and zinc salts. Acceptable base addition salts also include organic salts made from basic amines such as, for example, N,N'-dibenzylethylene-diamine, chloroprocaine, choline, diethanolamine, ethylenediamine, and procaine. All of these salts may be prepared from the corresponding compound by reacting, for example, the appropriate acid or base with the compound.

Kits

The present invention includes kits for treating or preventing conditions or improving physiological functions as described herein.

In one aspect, the invention includes a kit comprising meglumine or a salt thereof, and an instructional material which describes administering the meglumine or salt thereof or a composition comprising the meglumine or a salt thereof to a cell or an animal. Optionally the invention further includes a standard. This should be construed to include other embodiments of kits that are known to those skilled in the art, such as a kit comprising a (preferably sterile) solvent suitable for dissolving or suspending the composition of the invention prior to administering the compound to a cell or an animal. Preferably the animal is a mammal. More preferably, the mammal is a human.

Methods

The invention includes a method of ameliorating or preventing weight gain, promoting weight control, or promoting weight loss in a subject in need thereof. The method comprises administering to a subject an effective amount of a composition comprising meglumine or a salt thereof;

whereby weight gain in the subject is ameliorated or prevented, or weight control or weight loss in the subject is promoted.

The invention further includes a method of treating or preventing disregulation of blood glucose levels in a subject in need thereof. The method comprises administering to a subject an effective amount of a composition comprising meglumine or a salt thereof; whereby disregulation of blood glucose levels in the subject is treated or prevented.

The invention further includes a method of treating or preventing muscle weakness or increasing muscle strength in a subject in need thereof. The method comprises administering to a subject an effective amount of a composition comprising meglumine or a salt thereof; whereby muscle weakness in the subject is treated or prevented, or muscle strength in the subject is increased.

The invention further includes a method of reducing or preventing the increase of triglyceride levels in a subject in need thereof. The method comprises administering to a subject an effective amount of a composition comprising meglumine or a salt thereof; whereby the increase of triglyceride levels in the subject is reduced or prevented.

The invention further includes a method of reducing or preventing the increase of LDL levels in a subject in need thereof. The method comprises administering to a subject an effective amount of a composition comprising meglumine or a salt thereof; whereby the increase of LDL levels in the subject is reduced or prevented.

The invention further includes a method of reducing or preventing the increase of total cholesterol levels in a subject in need thereof. The method comprises administering to a subject an effective amount of a composition comprising meglumine or a salt thereof; whereby the increase of total cholesterol levels in the subject is reduced or prevented.

The invention further includes a method of reducing or preventing the increase of levels of a lipoprotein particle apolipoprotein in a subject in need thereof. The method comprises administering to a subject an effective amount of a composition comprising meglumine or a salt thereof; whereby the increase of levels of the lipoprotein particle or apolipoprotein in the subject is reduced or prevented.

The invention further includes a method of increasing or preventing the reduction of creatine/albumin levels in a subject in need thereof. The method comprises administering to a subject an effective amount of a composition comprising meglumine or a salt thereof, whereby the creatine/albumin levels in the subject are increased or the reduction of the creatine/albumin levels in the subject is prevented.

The invention further includes a method of increasing longevity or promoting anti-aging effects in a subject in need thereof. The method comprises administering to a subject an effective amount of a composition comprising meglumine or a salt thereof, whereby longevity in the subject is increased.

The invention further includes a method of improving the skin condition in a subject in need thereof. The method comprises administering to a subject an effective amount of a composition comprising meglumine or a salt thereof; whereby the skin condition in the subject is improved.

The invention further comprises a method of improving sexual stamina or performance in a subject in need thereof. The method comprises administering to a subject an effective amount of a composition comprising meglumine or a salt thereof; whereby sexual stamina or performance in the subject is improved.

The invention further comprises a method of increasing vitality or energy levels in a subject in need thereof. The method comprises administering to a subject an effective amount of a composition comprising meglumine or a salt thereof; whereby vitality or energy levels in the subject are increased.

The invention further comprises a method of improving the mental capacity, or ameliorating or preventing the onset of dementia, in a subject in need thereof. The method comprises administering to a subject an effective amount of a composition comprising meglumine or a salt thereof; whereby the mental capacity is improved, or the onset of dementia in the subject is ameliorated or prevented.

The invention further comprises a method of improving or maintaining kidney function in a subject in need thereof. The method comprises administering to a subject an effective amount of a composition comprising meglumine or a salt thereof; whereby kidney function in the subject is improved or maintained.

In one embodiment, the composition is administered to the subject by a route selected from the group consisting of inhalational, oral, rectal, vaginal, parenteral, topical, transdermal, pulmonary, intranasal, buccal, ophthalmic, intrathecal, parenteral, intravenous, and any combinations thereof. In another embodiment, the composition is administered to the subject at a frequency selected from the group consisting of once a day, twice a day, three times a day, four times a day, once a week, twice a week, three times a week, four times a week, once a month, twice a month, and any combinations thereof. In yet another embodiment, the composition is administered to the subject at a dosage ranging from about 1 ng/kg/application to about 100 g/kg/application. In yet another embodiment, the composition is administered to the subject at a dosage ranging from about 1 ng/kg/application to about 100 mg/kg/application. In yet another embodiment, the composition is administered to the subject as a controlled-release formulation. In yet another embodiment, the subject is a mammal. In yet another embodiment, the mammal is a human. In yet another embodiment, the subject is further administered medication to treat symptoms of diabetes. In yet another embodiment, the diabetes is type 2 diabetes. In yet another embodiment, the lipoprotein particle or apolipoprotein comprises Apo B, LDL-P, sdLDL, Apo A-I or any combinations thereof. In yet another embodiment, the lipoprotein particle or apolipoprotein comprises Apo B, and the Apo B:Apo A-I ratio in the subject is reduced.

Formulations

The compositions useful within the invention is in a form suitable for administration to a subject, or the composition may further comprise one or more acceptable carriers, one or more additional ingredients, or some combination of these. The meglumine may be present in the composition in the form of a physiologically acceptable salt, such as in combination with a physiologically acceptable cation or anion, as is well known in the art.

In an embodiment, the compositions useful for practicing the method of the invention may be administered to deliver a dose of between 1 ng/kg/day and 100 mg/kg/day. In another embodiment, the compositions useful for practicing the invention may be administered to deliver a dose of between 1 ng/kg/day and 500 mg/kg/day.

The relative amounts of the active ingredient, the acceptable carrier, and any additional ingredients in a composition of the invention varies, depending upon the identity, size, and condition of the subject treated and further depending upon the route by which the composition is to be administered. By way of example, the composition may comprise between 0.1% and 100% (w/w) active ingredient.

Compositions useful in the methods of the invention may be suitably developed for inhalational, oral, rectal, vaginal, parenteral, topical, transdermal, pulmonary, intranasal, buccal, ophthalmic, intrathecal, parenteral, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the condition being treated, the type and age of the veterinary or human patient being treated, and the like.

The formulations of the compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (for example, about 1 to 4 or more times per day). When multiple daily doses are used, the unit dosage form may be the same or different for each dose.

Although the descriptions of compositions provided herein are principally directed to non-toxic compositions suitable for ethical administration to humans, it is understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and perform such modification with merely ordinary, if any, experimentation. Subjects to which administration of the compositions of the invention is contemplated include, but are not limited to, humans and other primates, mammals including commercially relevant mammals such as cattle, pigs, horses, sheep, cats, and dogs.

In one embodiment, the compositions are formulated using one or more acceptable non-toxic excipients or carriers. In one embodiment, the compositions comprise an effective amount of meglumine and an acceptable carrier. Acceptable carriers, which are useful, include, but are not limited to, glycerol, water, saline, ethanol and other acceptable salt solutions such as phosphates and salts of organic acids. Examples of these and other acceptable carriers are described in Remington's Pharmaceutical Sciences, 1991, Mack Publication Co., New Jersey.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Formulations may be employed in admixtures with conventional excipients, i.e., acceptable non-toxic organic or inorganic carrier substances suitable for oral, parenteral, nasal, intravenous, subcutaneous, enteral, or any other suitable mode of administration, known to the art. The preparations may be sterilized and if desired mixed with auxiliary agents, for example, lubricants, preservatives, stabilizers, wetting agents, emulsifiers, salts for influencing osmotic pressure buffers, coloring, flavoring and/or aromatic substances and the like. They may also be combined where desired with other active agents, for example, other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and acceptable polymeric or hydrophobic materials. Other "additional ingredients" that may be included in the compositions of the invention are known in the art and described, for example, in Genaro, ed., 1985, Remington's Pharmaceutical Sciences, Mack Publishing Co., Easton, Pa., which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included, but are not limited to, those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent that inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (for example, disodium edetate) and citric acid in the weight range of about 0.01% to 0.20% and more preferably in the range of 0.02% to 0.10% by weight by total weight of the composition. The chelating agent is useful for chelating metal ions in the composition, which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (for example, polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one that comprises a carbon-containing liquid molecule and which exhibits a less polar character than water. Liquid solutions of the composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount. For example, the therapeutic formulations may be administered to the patient either prior to or after diagnosis of any of the condition s contemplated herein, or to affect or improve any of the physiological functions contemplated herein. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat the condition s contemplated herein in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the condition, age, sex, weight, condition, general health and prior medical history of the patient being treated, and like factors well-known in the art. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon any number of factors, such as, but not limited to, the type and severity of the condition being treated, and the type and age of the animal.

Actual dosage levels of the active ingredients in compositions of this invention may be varied so as to obtain an amount of the active ingredient that is effective to achieve the desired response for a particular patient, composition, and mode of administration, without being toxic to the patient.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of platelet hyperactivity in a patient.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from subject to subject depending on many factors including, but not limited to, age, condition to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments therebetween.

In some embodiments, the dose of a compound of the invention is from about 0.5 µg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged composition comprising a container holding a therapeutically effective amount of a compound of the invention, alone or in combination with a second agent; and instructions for using the compound to treat, prevent, or reduce the conditions contemplated herein in a patient.

The term "container" includes any receptacle for holding the composition. For example, in one embodiment, the container is the packaging that contains the composition. In other embodiments, the container is not the packaging that contains the composition, i.e., the container is a receptacle, such as a box or vial that contains the packaged composition or unpackaged composition and the instructions for use of the composition. Moreover, packaging techniques are well known in the art. It should be understood that the instructions for use of the composition may be contained on the packaging containing the composition, and as such the instructions form an increased functional relationship to the packaged product. However, it should be understood that the instructions may contain information pertaining to the compound's ability to perform its intended function, for example, treating, preventing, or reducing the conditions contemplated herein.

Routes of Administration

Routes of administration of any of the compositions of the invention include inhalational, oral, nasal, rectal, parenteral, sublingual, transdermal, transmucosal (for example, sublingual, lingual, (trans)buccal, (trans)urethral, vaginal (for example, trans- and perivaginally), (intra)nasal, and (trans) rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gel caps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic excipients suitable for the manufacture of tablets. Such excipients include, for example, an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for a non-toxic, elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with non-toxic acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (for example, OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with acceptable non-toxic additives such as suspending agents (for example, sorbitol syrup, methyl cellulose or hydrogenated edible fats); emulsifying agent (for example, lecithin or acacia); non-aqueous vehicles (for example, almond oil, oily esters or ethyl alcohol); and preservatives (for example, methyl or propyl para-hydroxy benzoates or sorbic acid). Liquid formulations of a non-toxic composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, an acceptable non-toxic carrier, and at least sufficient liquid to moisten the mixture. Acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active compound by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Parenteral Administration

As used herein, "parenteral administration" of a composition includes any route of administration characterized by physical breaching of a tissue of a subject and administration of the composition through the breach in the tissue. Parenteral administration thus includes, but is not limited to, administration of a composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a composition suitable for parenteral administration comprise the active ingredient combined with an acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (for example, sterile pyrogen-free water) prior to parenteral administration of the reconstituted composition.

The compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or diglycerides. Other parentally-administrable formulations useful include those which comprise the active ingredient in microcrystalline form, in a liposomal preparation, or as a component of a biodegradable polymer system. Compositions for sustained release or implantation may comprise acceptable non-toxic polymeric or hydrophobic materials such as an emulsion, an ion exchange resin, a sparingly soluble polymer, or a sparingly soluble salt.

Topical Administration

An obstacle for topical administration of compositions is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of compounds across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, polar lipids, or N-methyl-2-pyrrolidone.

One acceptable vehicle for topical delivery of some of the compositions of the invention may contain liposomes. The composition of the liposomes and their use are known in the art (for example, U.S. Pat. No. 6,323,219).

In alternative embodiments, the topically active composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

Buccal Administration

A composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating acceptable excipient which is solid at ordinary room temperature (i.e., about 20° C.) and which is liquid at the rectal temperature of the subject (i.e., about 37° C. in a healthy human). Suitable non-toxic acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a non-toxic acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Delivery Systems

Controlled- or sustained-release formulations of a non-toxic composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, may be readily selected for use with the compositions of the invention. Thus, single unit dosage forms suitable for oral administration, such as tablets, capsules, gel caps, and caplets, that are adapted for controlled-release are encompassed by the present invention.

Most controlled-release products have a common goal of improving therapy over that achieved by their non-controlled counterparts. Ideally, the use of an optimally designed controlled-release preparation in treatment is characterized by a minimum of substance being employed to cure or control the condition in a minimum amount of time. Advantages of controlled-release formulations include extended activity of the compound, reduced dosage frequency, and increased subject compliance. In addition, controlled-release formulations can be used to affect the time of onset of action or other characteristics, such as blood level of the compound, and thus can affect the occurrence of side effects.

Most controlled-release formulations are designed to initially release an amount of compound that promptly produces the desired therapeutic effect, and gradually and continually release of other amounts of compound to maintain this level of therapeutic effect over an extended period of time. In order to maintain this constant level of compound in the body, the compound must be released from the dosage form at a rate that will replace the amount of compound being metabolized and excreted from the body.

Controlled-release of an active ingredient can be stimulated by various inducers, for example, pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a formulation that provides for gradual release of a compound over an extended period of time, and that may, although not necessarily, result in substantially constant blood levels of a compound over an extended time period. The period of time may be as long as a month or more and should be a release which is longer that the same amount of agent administered in bolus form. For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a patient, alone or in combination with another agent, using a sustained release formulation.

The term delayed release is used herein in its conventional sense to refer to a formulation that provides for an initial release of the compound after some delay following compound administration and that mat, although not necessarily, includes a delay of from about 10 minutes up to about 12 hours. The term pulsatile release is used herein in its conventional sense to refer to a formulation that provides release of the compound in such a way as to produce pulsed plasma profiles of the compound after compound administration. The term immediate release is used in its conventional sense to refer to a formulation that provides for release of the compound immediately after compound administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after compound administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after compound administration.

In accordance with the present invention, as described above or as discussed in the Examples below, there can be employed conventional chemical, cellular, histochemical, biochemical, molecular biology, microbiology and recombinant DNA techniques which are known to those of skill in the art. Such techniques are explained fully in the literature. See for example, Sambrook et al., 1989 Molecular Cloning—a Laboratory Manual, Cold Spring Harbor Press; Glover, (1985) DNA Cloning: a Practical Approach; Gait, (1984) Oligonucleotide Synthesis; Harlow et al., 1988 Antibodies—a Laboratory Manual, Cold Spring Harbor Press; Roe et al., 1996 DNA Isolation and Sequencing: Essential Techniques, John Wiley; and Ausubel et al., 1995 Current Protocols in Molecular Biology, Greene Publishing.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Grip Strength Test

The grip strength test is a widely-used non-invasive method designed to evaluate mouse limb strength that has been used to investigate the effects of neuromuscular disorders and compound under testing. It is based on the natural tendency of the mouse to grasp a bar or grid when it is suspended by the tail. During this test the mouse grips with both forelimbs (or hind-limbs) a single bar or a mesh.

There are three kinds of grip strength tests used: Mesh Grip Test, Wire Grip Test, and Automatic Grip Strength (GS Meter). The Mesh Grip Test measures the ability of the mouse to remain clinging to an inverted or tilted surface such as a wire grid or a cage lid for a period of time, usually up to 1 minute; the Wire Grip Test measures the ability of the mouse to hang on a wire with its forepaws for a preset length of time or until grip fails, while in the Automatic Grip Strength the mouse grasps a horizontal metal bar or grid while is pulled by the tail. The bar or grid is attached to a force transducer that peak pull-force achieved on its digital display.

This method can be used to measure condition progression and neurobehaviour as well as to test effect of specific therapeutic interventions in mouse models of neuromuscular disorders; increases in grip strength have been interpreted as evidence of increased muscle strength.

The grip strength test is useful to assess strength in animal models of spinal muscular atrophy (SMA) and the effect of experimental therapies. This test can be performed reliably in SMA mice starting at 2-4 weeks of life (mesh grip≥postnatal day 12 (P12); bar test≥P10; automated≥P28). Since this is an in vivo behavioural test, by its nature, it has variability. In carefully controlled conditions, the variability within a group of animals of similar gender, age, and genotype should range between 10-25%. A similar variability should be observed among repeated measures (3 to 5) performed in the same animal during the trial.

Example 1

Mice Study

A group of sixteen C57BL/6 male mice at 12 weeks of age were distributed into 4 groups (n=4 each). Animals were fed a normal diet supplemented with 0 mM, 10 mM, 40 mM, or 75 mM meglumine in the drinking water. The approximate doses of meglumine were 537 mg/kg/day, 2,146 mg/kg/day, and 4,027 mg/kg/day for animals treated with, respectfully, 10 mM, 40 mM and 75 mM meglumine.

Animals were observed daily, and date of death was noted if applicable. Four animals were found dead in their cages, and twelve were euthanized after showing symptoms of distress (hunched posture, weight loss, decreased food intake).

Animal Weights:

Animals were weighed weekly, and their average weight is illustrated in FIG. 1. For all groups, animals gained weight from weeks 12-52, maintained a relatively stable weight from weeks 42-84, and decreased weight after week 92. Certain animals showed marked weight loss just prior to death. The group that received water without meglumine weighed slightly less than the animals in the meglumine treated groups at the start of the study, and this persisted for the study duration. Animals treated with meglumine weighed more than the controls, but the increase was not dose-dependent.

Figure 2:
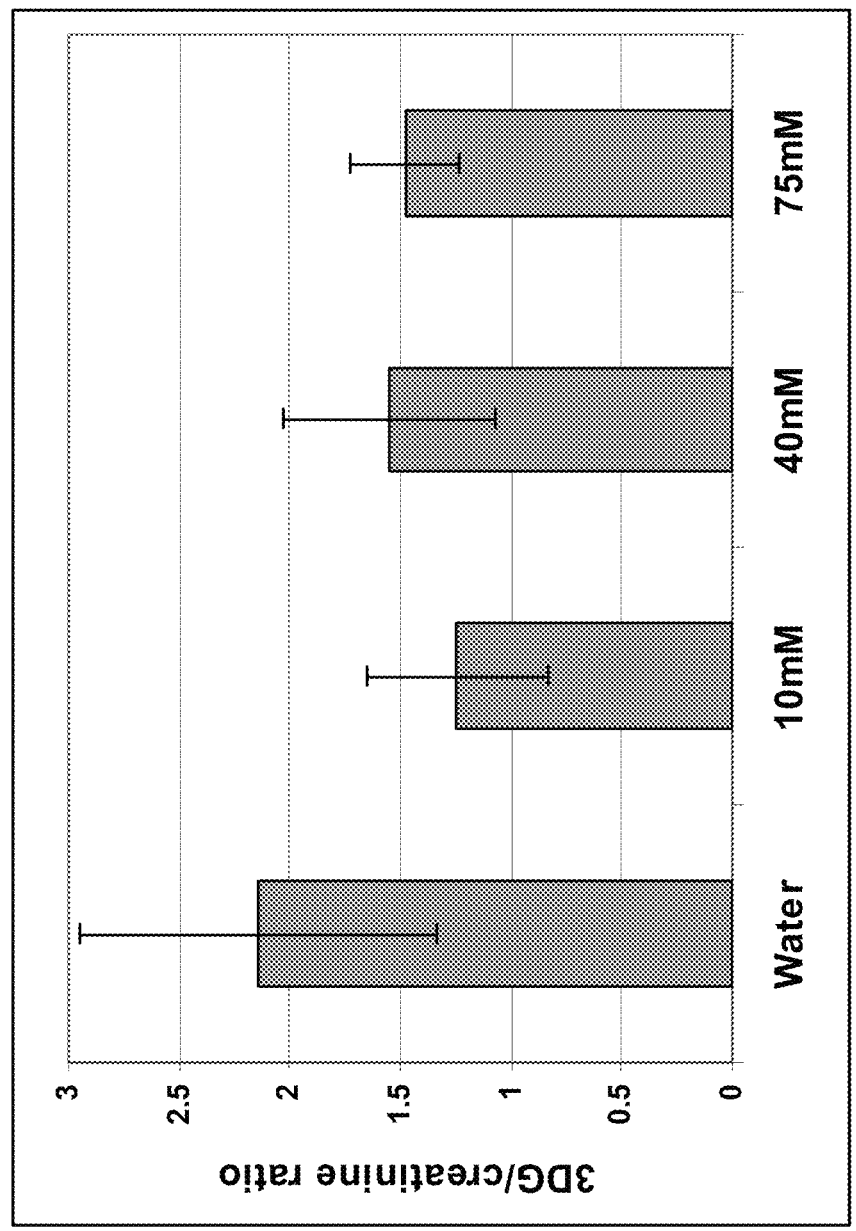
FIG. 2 is a graph illustrating the measured 3DG/creatine ratio for mice treated with various doses of meglumine.

Urine 3-Deoxyglucosone (3DG) Levels:

Urine was collected from animals (n=3 for all groups, except n=4 for 75 mM meglumine) at the age of 103 weeks and 3DG levels were measured using GC-MS with an internal U-[$^{13}$C]-3DG standard (FIG. 2). Prior to analysis, urine samples were treated with 2,3-diaminonapthalene overnight to derivatize 3DG, and then extracted with ethyl acetate. Urinary creatinine levels were measured with a reagent kit from Oxford Biochemicals. The 3DG/creatinine ratio (±standard deviation) is illustrated in FIG. 2. The ratio for all meglumine treated animals was less than the control animals.

Longevity:

The average lifespan (±standard deviation) for the mice treated with 0 mM, 10 mM, 40 mM and 75 mM meglumine was 771±214.6 days, 834±124 days, 927±80.3 days and 1,027±117.5 days. Animals treated with 10 mM, 40 mM and 75 mM lived, respectively, 8.2%, 20.2%, and 33.2% longer than the control animals.

Example 2

Rat Study

Eighteen male Sprague-Dawley rat (ACE) weighing 150-175 g were divided into 3 groups (n=6) and fed a normal diet supplemented with 0 mM, 25 mM, or 75 mM meglumine in the drinking water for 32 weeks.

Advanced Glycation End Product in Skin:

At the end of 32 weeks the ratio of advanced glycation end products (AGE products) to total protein was determined in the skin using the ratio of fluorescence measurements. A 3 cm² biopsy was taken from the shaved dorsal surface of the rats. The dermis was separated from the epidermis via immersion in water at 55° C. for 30 seconds, followed by gentle scraping of epidermis. The dermis was placed onto a wire screen cut to fit diagonally into fluorescence spectrometer. Fluorescence was recorded on PE 650-40 fluorescence spectrometer using front surface ("diagonal") geometry. Fluorescence intensities were monitored at excitation/emission wavelengths of 270/300 nm, 270/330 nm, 270/360 nm, 270/400 nm, 325/400 nm, 270/450 nm and 370/450 nm. For direct comparison at the same excitation wavelength, ratios of I(270/330 nm) to I(270/450 nm) were recorded. These ratios were corrected for different instrumental responses at 330 and 450 nm.

Figure 3:
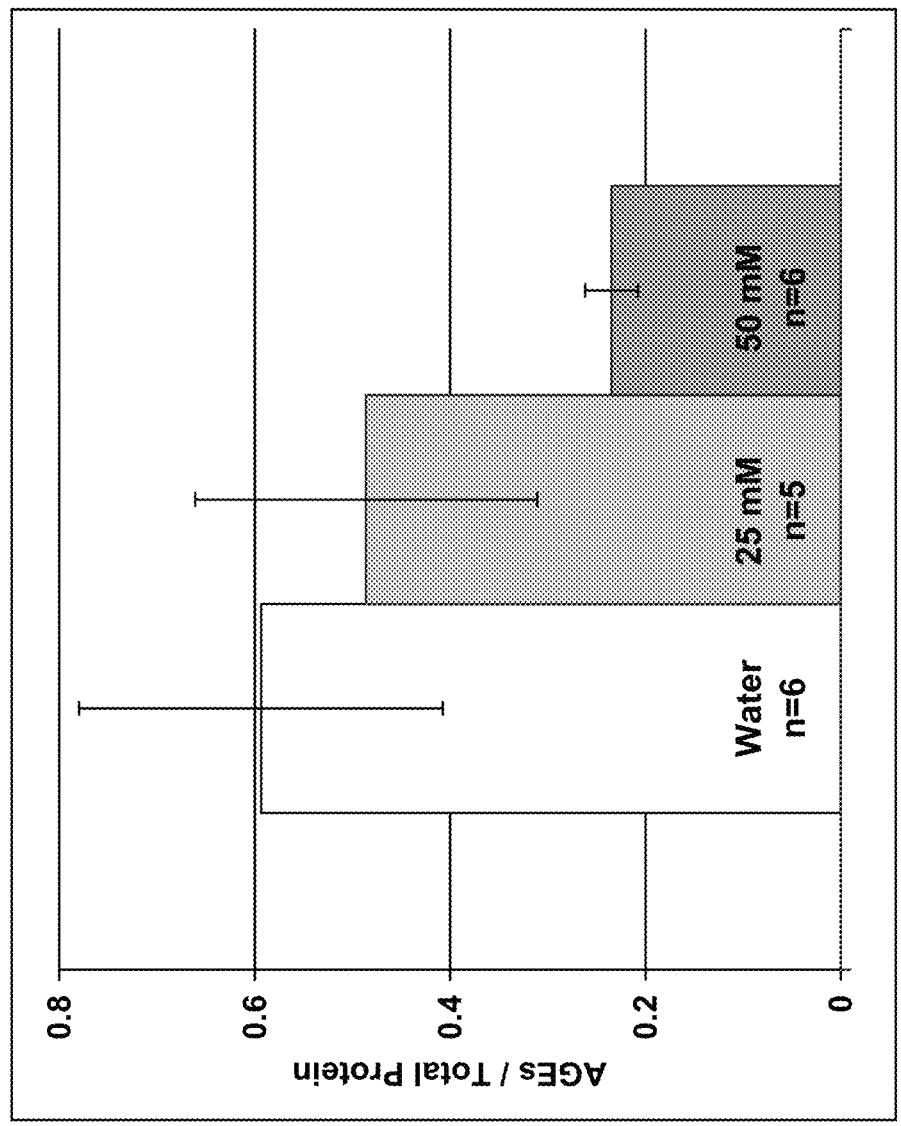
FIG. 3 is a graph illustrating the amount of AGE products identified in the skin of rats treated with meglumine for 32 weeks.

The amount of skin AGE products in each of the three cohort groups at 32 weeks is illustrated below in Table 1 and FIG. 3; the larger the ratio, the more AGEs were present in the skin. The amount of AGE product in the skin observed in untreated rats decreased by 10% with 25 mM meglumine and 60% with 50 mM meglumine (FIG. 3). However, the trends did not reach statistical significance.

TABLE 1

Statistical analyses of AGE products in skin of meglumine treated rats for 32 weeks.

|  | Water | 25 mM Meg | 50 mM Meg |
|---|---|---|---|
| Mean AGE/Total Protein | 0.594 ± 0.173 | 0.486 ± 0.187 | 0.235 ± 0.067 |
| P value (treated vs untreated) |  | 0.686 | 0.086 |

Urinary 3DG Levels:

The level of 3DG was measured in the urine of the rats at 32 weeks. 3DG levels were measured by GC-MS by reacting 0.1 ml of sample, to which 20 picomoles of [U-$^{13}$C] labeled 3DG had been added as an internal standard, with 1 ml of 1 mM 2,3-diaminonaphthalene (DAN) for 24 hours at room temperature.

Following reaction with DAN, the sample was extracted with four volumes of ethyl acetate and then dried. The residue was dissolved in 50 μl of N-methyl-N-(trimethylsilyl)trifluoroacetamide and heated at 65° C. for 30 min. 2 μl was analyzed by GC-MS. Levels of 3DG were normalized to creatinine levels measured with reagents from Oxford Biochemicals.

Figure 4:
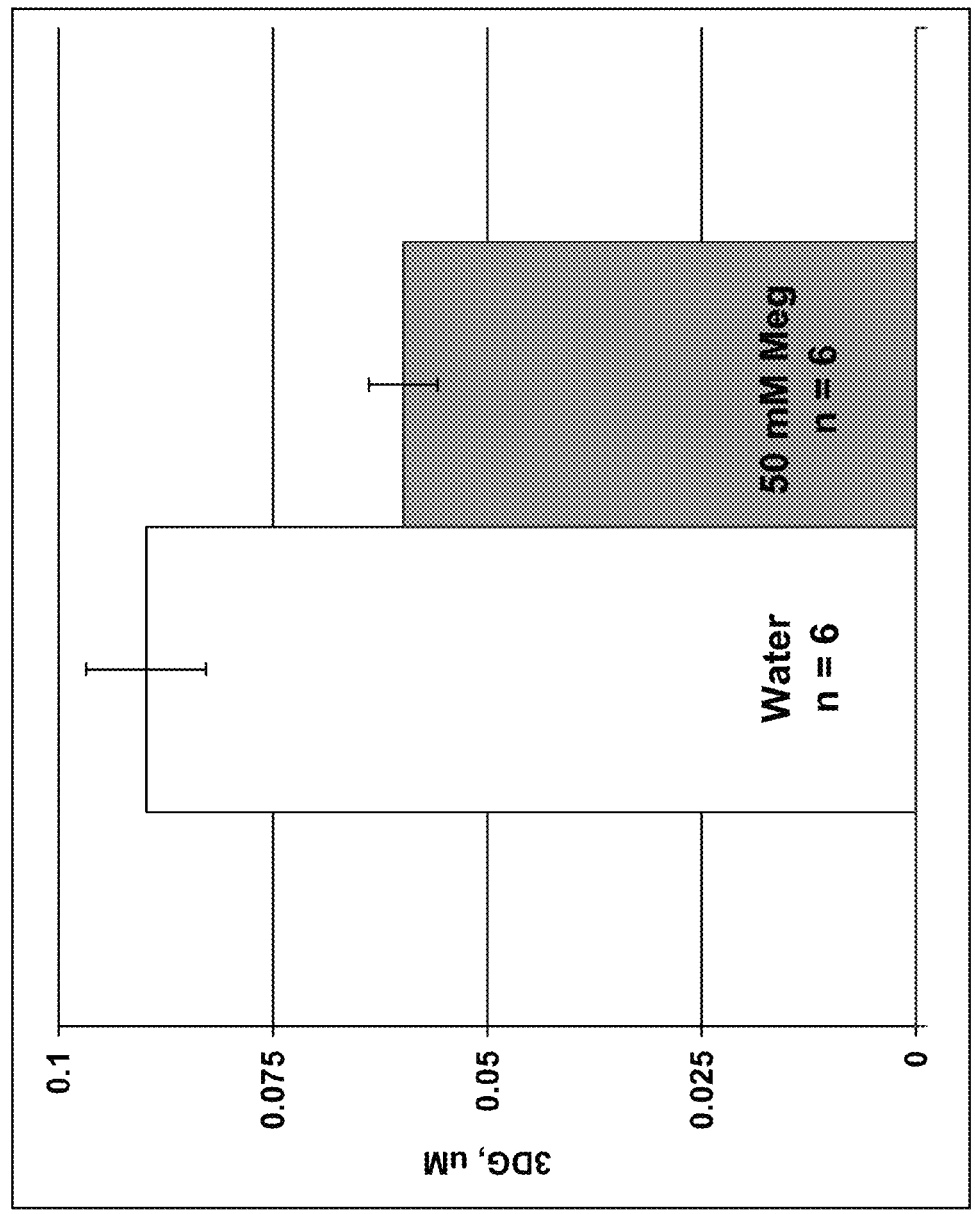
FIG. 4 is a graph illustrating the urinary 3DG levels in rats treated with meglumine for 32 weeks.

After 32 weeks, 3DG levels were measured in the urine of rats on water and treated with 50 mM meglumine. 3DG levels were 33% lower in rats treated with 50 mM meglumine (FIG. 4) and Table 2. This difference reached statistical significance of <0.005.

TABLE 2

Statistical analyses of urinary 3DG levels in meglumine treated rats for 32 weeks.

|  | Water | 50 mM Meg |
|---|---|---|
| 3DG, uM | 0.0891 ± 0.007 | 0.0598 ± 0.004 |
| P value (treated vs untreated) |  | 0.005 |

Urinary Isoprostane Levels:

Rat urine from 32 weeks was measured for the presence of isoprostane, a marker for oxidative stress using a competitive ELISA (Oxford Biochemicals, Oxford Mich.). All values were normalized to creatinine levels to control for differences in urine volume. Creatinine was measured using a kit from Oxford Biochemicals.

Figure 5:
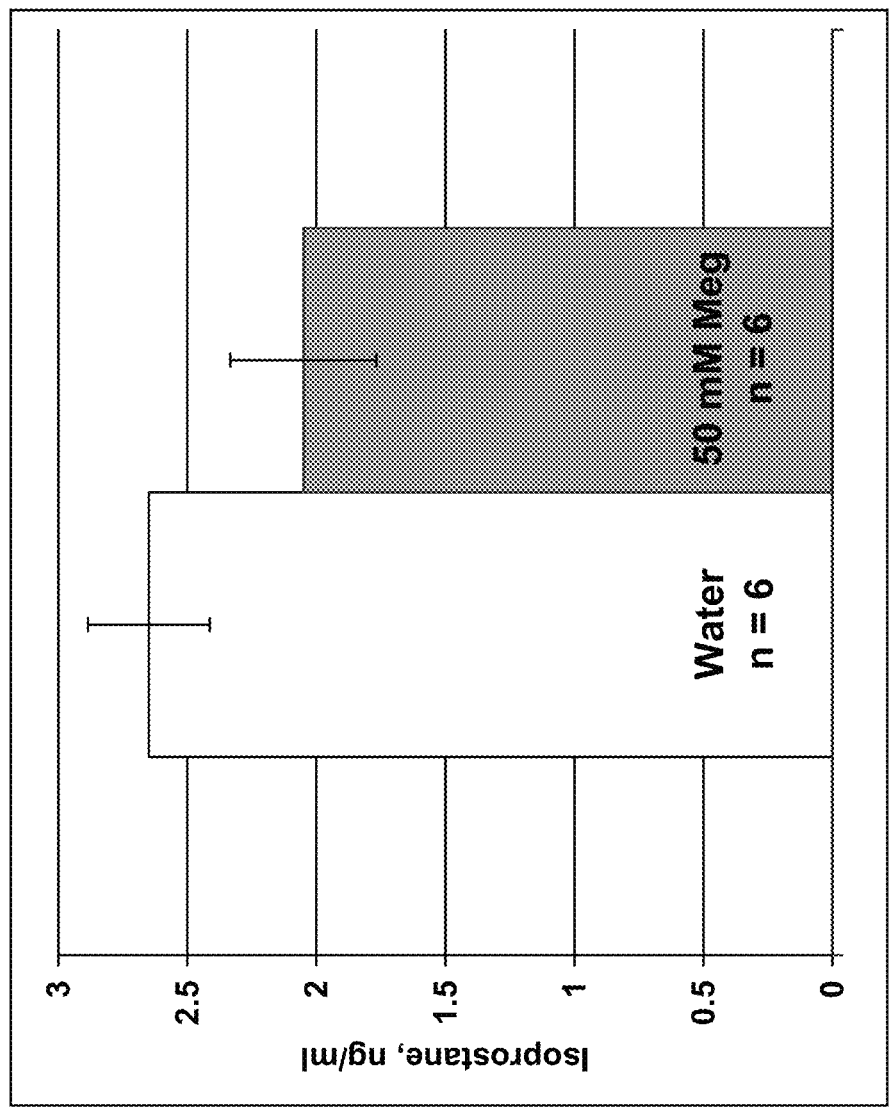
FIG. 5 is a graph illustrating the urinary isoprostane levels in rats treated with meglumine for 32 weeks.

After 32 weeks, isoprostane levels were measured in the urine of rats on water and treated with 50 mM meglumine. As illustrated in FIG. 5 and Table 3, isoprostane levels were 22% lower in rats treated with 50 mM meglumine. However this trend did not reach statistical significance.

TABLE 3

Statistical analyses of urinary isoprostane levels in meglumine treated rats for 32 weeks.

|  | Water | 50 mM Meg |
|---|---|---|
| Isoprostane, ng/ml | 2.65 ± 0.236 | 2.05 ± 0.283 |
| P value (treated vs untreated) |  | 0.136 |

3DG Adduct Levels in Skin

The presence of imidazolone, a 3DG-derived adduct formed from the reaction of 3DG and arginine was measured by fluorescent immunohistochemistry, using a monoclonal antibody to imidazolone, AG-1 (T.Niwa).

A piece of skin from each rat on water and 50 mM meglumine was fixed in formalin, and thin sections were treated with AG-1 antibody and then a fluorescent second antibody, and each slide was scanned using a fluorescence microscope. The total florescence due to imidazolone over each slide was measured.

Figure 6:
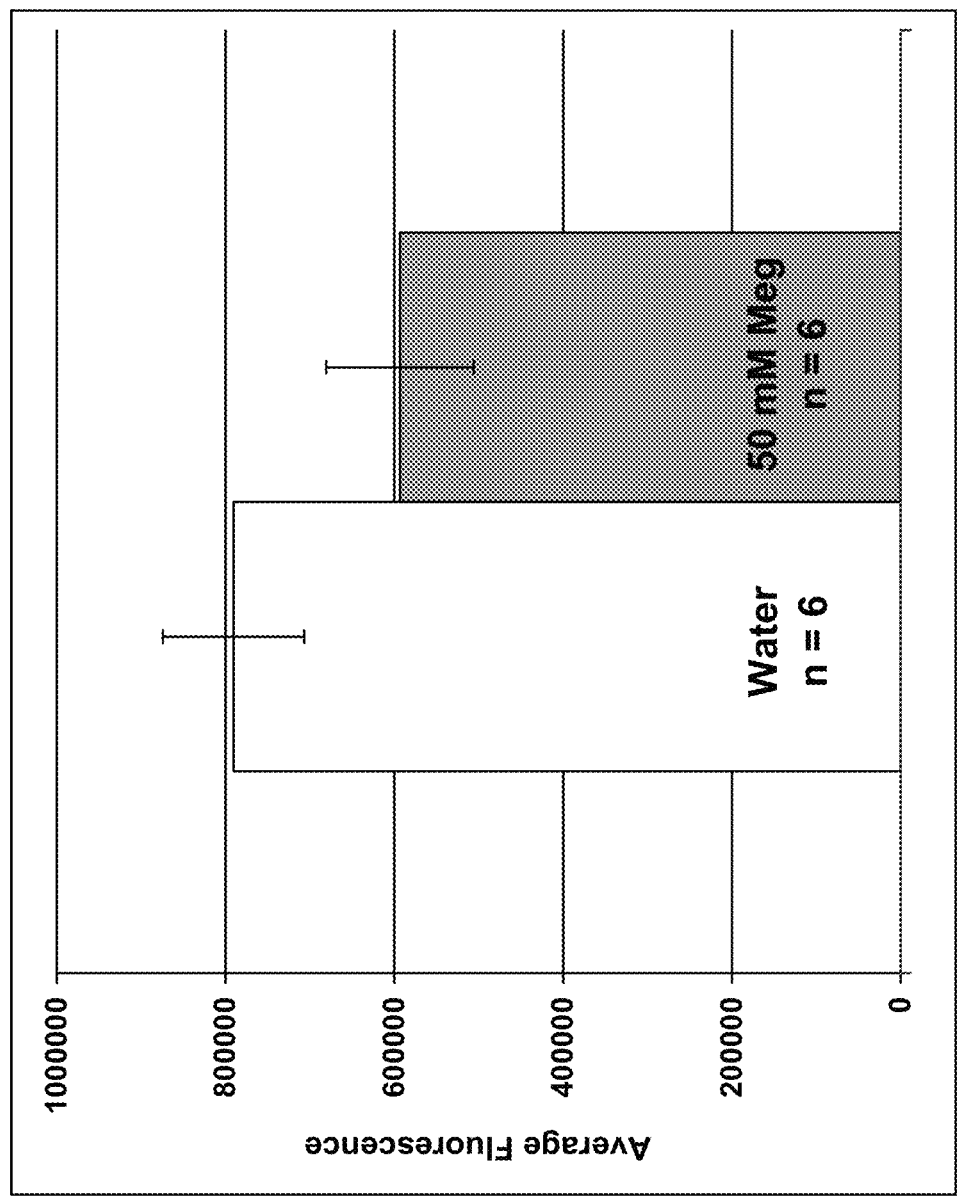
FIG. 6 is a graph illustrating the measurement of 3DG imidazolone in the skin of rats treated with meglumine for 32 weeks.

The average fluorescence for skins of rats treated with water or 50 mM meglumine. Rats on meglumine had 25% less imidazolone in their skin (FIG. 6) and Table 4, although the difference was not statistically significant.

TABLE 4

Statistical analysis of 3DG adducts levels in skin of meglumine treated rats for 32 weeks.

|  | Water | 50 mM Meg |
|---|---|---|
| Fluorescence | 790567 ± 83833 | 593320 ± 87404 |
| P value (treated vs untreated) |  | 0.134 |

3DG Adduct Levels in Kidney Tubules and Glomeruli:

The 3DG adduct imidazolone was measured in kidney tubules and glomeruli by fluorescent immunohistochemistry using a monoclonal antibody to imidazolone, AG-1 (T. Niwa). Kidneys from each rat on water or 50 mM meglumine were placed in formalin, and thin sections were prepared. Each slide was treated with AG-1 and then a fluorescent second antibody, and then scanned using a fluorescence microscope. The total florescence due to imidazolone over each structure measured.

Figure 7:
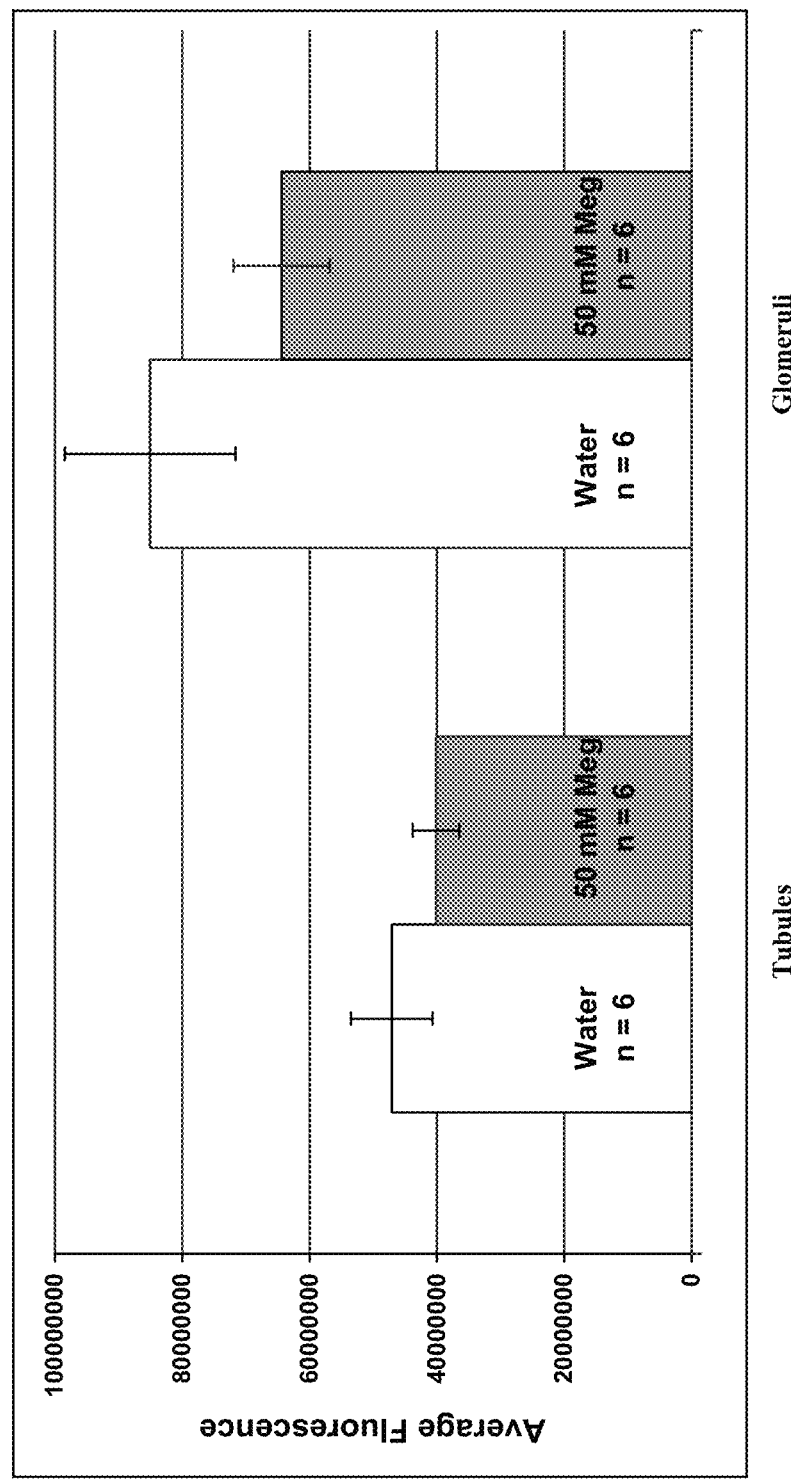
FIG. 7 is a graph illustrating the average fluorescence measured in the kidney tubules and glomeruli of rats treated with meglumine for 32 weeks.

The average fluorescence for tubules and glomeruli of rats treated for 32 weeks with water or 50 mM meglumine is illustrated in FIG. 7 and Table 5. Rats on meglumine had 13% less imidazolone in their tubules, although the difference was not statistically significant. Similarly, rats on meglumine had 24% less imidazolone in their glomeruli although again the difference was not statistically significant.

TABLE 5

Statistical analysis of 3DG adducts levels in tubules
and glomeruli of meglumine treated rats for 32 weeks.

|  | Water | 50 mM Meg |
|---|---|---|
| Fluorescence in Tubules | 47,081,228 ± 6,407,142 | 40,158,431 ± 3,644,819 |
| P value Tubules |  | 0.369 |
| Fluorescence in Glomeruli | 85,039,251 ± 13,401,970 | 64,376,501 ± 7,548,981 |
| P value Glomeruli |  | 0.2 |

Example 3

Glucose Tolerance Test

Figure 8:
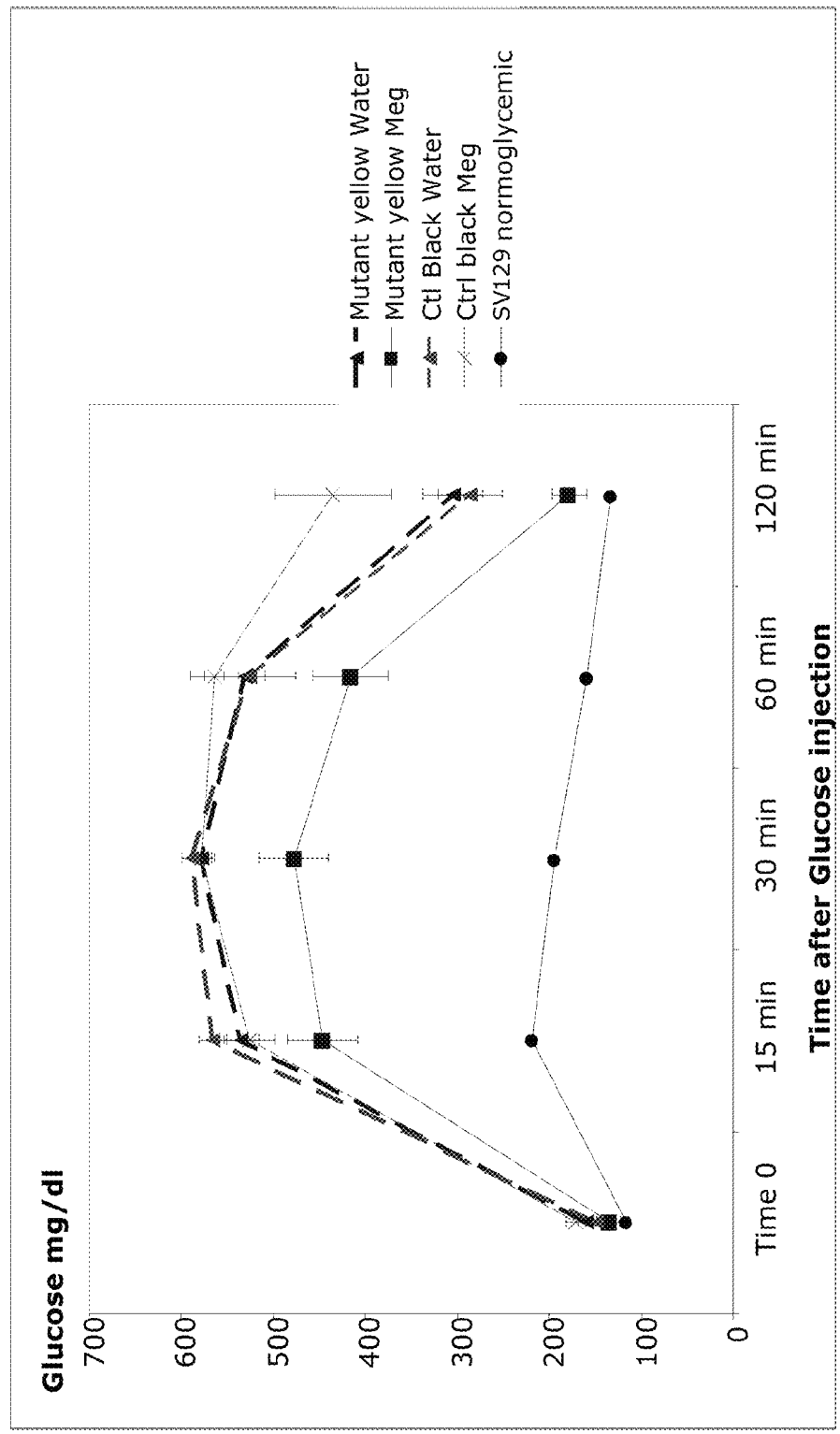
FIG. 8 is a graph of an oral glucose tolerance test in mice treated with no meglumine or various doses of meglumine.

Mutant KK.Cg-$A^{y/+}$/J "yellow mice" (which are prone to developing diabetes and obesity) and control KK.Cg-$A^{+/+}$/J "black mice" were fed with water or water supplemented with 18 mM meglumine hydrochloride for 16 weeks. As a comparison group, SV129 normoglycemic mice were fed with water. The animals were then fasted overnight and blood glucose measured (time 0 min). The animals were injected with glucose, and blood glucose levels measured after 15 min, 30 min, 60 min and 120 min. The results are illustrated in FIG. 8.

The mutant yellow mice that were treated with meglumine showed decreased blood glucose levels at 15 min, 30 min, 60 min and 120 minutes as compared to those treated with water.

Triglyceride Levels

Serum triglyceride levels were measured in KK.Cg-$A^{y/+}$/J diabetic mice treated with 18 mM meglumine hydrochloride in the drinking water for 32 weeks. The control animals (n=10) had an average of 752.21±2 01.29 mg/dL and the meglumine treated animals (n=9) had an average of 322.66±158.85 mg/dL. A t-test was used to compare the mean values and a p<0.001 was calculated, indicating the decrease in plasma triglycerides in the meglumine treated mice is statistically significant.

Urinary Albumin/Creatinine

Urinary creatinine and albumin levels were measured in KK.Cg-$A^{y/+}$/J "mutant" diabetic mice and KK.Cg-$A^{+/+}$/J "control" mice treated with or without 18 mM meglumine hydrochloride in the drinking water for 12 weeks. The control mice had an albumin/creatinine ratio of 2.5±1.2 (n=6), and the control mice treated with meglumine had a ratio of 1.6±1.8 (n=6). The mutant mice had a ratio of 17.3±15.4 (n=6) and the mutant mice treated with meglumine had a ratio of 12.4±8.7 (n=6). For both control and mutant animals, meglumine treatment resulted in a decreased ratio, and a t-test comparison of the mean values did not indicate the difference was significant.

Example 4

Strength Testing in Mice

A group of SV129 mice (n=15) and a group of mice treated with 18 mM meglumine hydrochloride in their drinking water (n=15) for 6 weeks were tested for the ability to hold on to an inverted metal grid. The length of time before falling off the grid was averaged, and the standard error was calculated.

The length of time that the animals could hold on to the grid was 6.3±3.4 seconds for the control group and 17.8±0.6 seconds for the meglumine group. A t-test comparison of the mean values was used to determine a p value=0.0006, indicating the results are significant.

Example 5

Effects of Meglumine in a Human Subject

A 59.5 year-old male suffering from right knee joint pain, and otherwise in good health, was orally administered 500-1,500 mg of meglumine hydrochloride on a daily basis over the period of 5 years (with two months off).

Over the period of the experiment, the subject experienced an overall weight loss/control effect, with an increase in muscle-to-fat index, strengthening of leg muscles and an increase of 1 inch in arm diameter. The subject further experienced improved muscle strength: he increased his military press weights from 200 lb to 355 lb, and was able to do crunches with 100 kgs sets of 25×4.

The subject's skin condition also improved, with the skin feeling smooth and well hydrated, and without development of age spots or wrinkles. The subject also experienced improved sexual stamina and sexual performance, with erections lasting for hours.

The subject experienced improved vitality or energy levels, performing hard work functions for up to 9 hours consistently. The subject's reflexes became quicker, and his olfaction senses were heightened.

The subject experienced increased mental capacity, with improvements in memory and development of vivid and detailed dreams. The subject described feeling as mentally active as a teenager.

Example 6

Effects of Meglumine in a Human Subject

A 83 year-old female suffering from high blood pleasure was orally administered meglumine hydrochloride on a daily basis over the period of one month.

Over the period of the experiment, the subject's blood pressure was reduced from 220/110 to normal range (around 130/78).

The subject experience better sleep and felt more energetic. The subject also experienced weight loss, losing at least one dress size.

Example 7

Effects of Meglumine in a Human Subject

A 76 year-old female on a blood thinner medication was orally administered meglumine hydrochloride on a daily basis over the period of 1 month. After that period she was able to discontinue the use of the blood thinner.

Example 8

Effects of Meglumine in a Human Subject

A 46 year-old male was overweight and suffering from fatty liver, experienced sore joints, lacked energy and required extended recovery time after exercise & travel, was orally administered 500-1,500 mg of meglumine hydrochloride on a daily basis over the period of 14 months.

Over the period of the experiment, the subject experienced an overall weight loss/control effect, with a reduction in weight on average from 108 kg to 102 kg, at approximately 0.5 kg lost per month. The subject further experienced improved muscle strength and substantial strength increase ("about 100 lbs stronger than when I was 25 years old playing high level sports").

The subject's skin condition also improved, with a visually noticeable marked improvement in entire skin condition both in reduction of sun spots & texture (softening). The subject also experienced improved sexual stamina and sexual performance.

The subject experienced improved vitality or energy levels, including overall reflexes and ability of recovering from travel and exercise.

The subject experienced increased mental capacity, with improvement in memory, retention of data, concentration levels and problem solving.

The subject also experienced improvement in nail and hair health.

Example 9

Effects of Meglumine in a Human Subject

A 41 year-old female suffering from high blood sugar was orally administered meglumine hydrochloride on a daily basis over the period of 7 months.

Over the period of the experiment, the subject experienced an overall weight loss/control effect, with loss of 25 pounds without regain of the lost weight. The subject further experienced a decrease in blood glucose level from 202 to 75 mg/dL.

The subject experienced improved vitality or energy levels, including overall reflexes and ability of recovering from travel and exercise.

The subject's skin condition also improved, with the skin feeling softer and more blemish free.

The subject also experienced dramatically improved sexual stamina and sexual performance.

The subject experienced improved vitality or energy levels, with the ability of using heavier weights when working out and recovering faster from exhaustive activities.

The subject experienced increased mental capacity, feeling more focused and with better reasoning skills.

The subject also experienced improvement in nail and hair health.

Example 10

Effects of Meglumine in a Human Subject

A 69-year-old woman, suffering from scleroderma and type 2 diabetes, overweight and with difficulty to lose through dieting and exercise, experiencing less energy than when younger, was administered meglumine hydrochloride (500 mg to 2000 mg) orally almost every day over 5 years.

The subject lost over 30 pounds over the first two and one half years without dieting or increasing exercise activity. The subject was able to maintain her weight.

The subject's blood glucose level improved upon being administering the compound (at a minimum dose of 500 mg three times a day). Her insulin and creatine/albumin levels are normal.

The subject's cholesterol levels went from 300 to 265 without diet change or any medicines. Her LDL level went from 209 to 160 within the last 16 months; her HDL levels stayed the same. Her CRP level went down (from 0.58 to <0.3), and so did her Lp-PLA level. Her fibrinogen homocysteine levels stayed the same.

The subject's overall energy levels have increased and the subject's massage therapist stated that the subject's limbs were more flexible and the subject was able to stretch more. The subject's appearance is younger, and her overall skin tone and texture have improved. The subject's mental capacity has not deteriorated over the period of testing. The subject's eye sight has improved over that period.

Example 11

Effects of Meglumine in a Human Subject

A 68-year-old woman, suffering from type 2 diabetes, overweight (height of 5 feet 1 inch, and weight of 129 pounds, as of month 0) and with difficulty to lose weight through dieting and exercise, was administered meglumine hydrochloride (3×500 mg) orally over the period of 8 months. Over the duration of the study the subject was also administered metformin orally to manage her type 2 diabetes.

The subject's blood was analyzed for lipids, lipoprotein particles and apolipoproteins, and inflammation/oxidation markers. The results are summarized in Table 6.

TABLE 6

| Class | Subclass | Reading month 0 | Reading month 8 |
|---|---|---|---|
| Lipids (mg/dL) | total cholesterol | 265 | 205 |
| | LDL-C direct | 160 | 111 |
| | HDL-C | 69 | 71 |
| | triglycerides | 135 | 82 |
| | non-HDL-C (calculated) | 196 | 134 |
| Lipoprotein Particles and Apolipoproteins | Apo B (mg/dL) | 133 | 79 |
| | LDL-P (nmol/L) | 2,250 | 1,529 |
| | sdLDL-C (mg/dL) | 56 | 28 |
| | % sdLDL-C (calculated) | 35 | 25 |
| | Apo A-I (mg/dL) | 183 | 176 |
| | HDL-P (μmol-L) | 44.3 | 43.7 |
| | HDL2-C (mg/dL) | 19 | 22 |
| | Apo B:Apo A-I ratio (calculated) | 0.73 | 0.45 |
| | Lp(a) mass (mg/dL) | 5 | 6 |
| Inflammation/ Oxidation | Lp-PLA$_2$ (ng/mL) | 152 | 172 |
| | hs-CRP (mg/L) | <0.3 | 0.3 |
| | fibrinogen (mg/dL) | 332 | 334 |

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating muscle weakness or increasing muscle strength in a subject in need thereof, the method comprising administering to the subject an effective amount of meglumine or a salt thereof as the single active agent; whereby administration of the meglumine or salt thereof treats muscle weakness in the subject, or increases muscle strength in the subject, and wherein the meglumine salt is formed between meglumine and an acid selected from the group consisting of sulfate, hydrogen sulfate, hydrochloric, hydrobromic, hydriodic, nitric, carbonic, sulfuric, phosphoric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic, methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, and galacturonic acid.

2. The method of claim 1, wherein the meglumine or salt thereof is administered to the subject by a route selected from the group consisting of inhalational, oral, rectal, vaginal, parenteral, topical, transdermal, pulmonary, intranasal, buccal, ophthalmic, intrathecal, parenteral, intravenous, and any combinations thereof.

3. The method of claim 1, wherein the meglumine or salt thereof is administered to the subject at a frequency selected from the group consisting of once a day, twice a day, three times a day, four times a day, once a week, twice a week, three times a week, four times a week, once a month, twice a month, and any combinations thereof.

4. The method of claim 1, wherein the meglumine or salt thereof is administered to the subject at a dosage ranging from about 1 ng/kg/application to about 100 g/kg/application.

5. The method of claim 4, wherein the meglumine or salt thereof is administered to the subject at a dosage ranging from about 1 ng/kg/application to about 100 mg/kg/application.

6. The method of claim 1, wherein the meglumine or salt thereof is administered to the subject as a controlled-release formulation.

7. The method of claim 1, wherein the subject is a mammal.

8. The method of claim 7, wherein the mammal is a human.

9. A method of treating muscle weakness or increasing muscle strength in a subject in need thereof, the method comprising administering to the subject an effective amount of meglumine or a salt thereof and a sweet tasting compound; whereby administration of the meglumine or salt thereof treats muscle weakness in the subject, or increases muscle strength in the subject, and wherein the meglumine salt is formed between meglumine and an acid selected from the group consisting of sulfate, hydrogen sulfate, hydrochloric, hydrobromic, hydriodic, nitric, carbonic, sulfuric, phosphoric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic, methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, and galacturonic acid.

10. The method of claim 9, wherein the meglumine or salt thereof is administered to the subject by a route selected from the group consisting of inhalational, oral, rectal, vaginal, parenteral, topical, transdermal, pulmonary, intranasal, buccal, ophthalmic, intrathecal, parenteral, intravenous, and any combinations thereof.

11. The method of claim 9, wherein the meglumine or salt thereof is administered to the subject at a frequency selected from the group consisting of once a day, twice a day, three times a day, four times a day, once a week, twice a week, three times a week, four times a week, once a month, twice a month, and any combinations thereof.

12. The method of claim 9, wherein the meglumine or salt thereof is administered to the subject at a dosage ranging from about 1 ng/kg/application to about 100 g/kg/application.

13. The method of claim 12, wherein the meglumine or salt thereof is administered to the subject at a dosage ranging from about 1 ng/kg/application to about 100 mg/kg/application.

14. The method of claim 9, wherein the meglumine or salt thereof is administered to the subject as a controlled-release formulation.

15. The method of claim 9, wherein the subject is a mammal.

16. The method of claim 15, wherein the mammal is a human.

* * * * *